(12) United States Patent  (10) Patent No.: US 8,617,195 B2
Ruan et al.  (45) Date of Patent: Dec. 31, 2013

(54) LANCING DEVICE

(75) Inventors: Tieming Ruan, Randolph, NJ (US);
Scott Hoover, Goshen, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 990 days.

(21) Appl. No.: 11/989,085

(22) PCT Filed: Aug. 3, 2006

(86) PCT No.: PCT/US2006/030180
§ 371 (c)(1),
(2), (4) Date: Jan. 28, 2011

(87) PCT Pub. No.: WO2007/019202
PCT Pub. Date: Feb. 15, 2007

(65) Prior Publication Data
US 2011/0118771 A1    May 19, 2011

Related U.S. Application Data

(60) Provisional application No. 60/705,349, filed on Aug. 4, 2005.

(51) Int. Cl.
*A61B 17/32* (2006.01)

(52) U.S. Cl.
USPC ...................................... 606/182

(58) Field of Classification Search
USPC .......... 606/167, 181–183, 185–189; 600/573, 600/583; 604/110, 136–138; 30/151, 30/335–339
See application file for complete search history.

(56) References Cited

U.S. PATENT DOCUMENTS

| 3,797,488 | A | 3/1974 | Hurschman et al. | 128/218 F |
|---|---|---|---|---|
| 4,203,446 | A | 5/1980 | Höfert et al. | 128/329 R |
| 4,442,836 | A | 4/1984 | Meinecke et al. | 128/314 |
| 4,449,529 | A | 5/1984 | Burns et al. | 128/314 |
| 4,469,110 | A | 9/1984 | Slama | 128/770 |
| 4,517,978 | A | 5/1985 | Levin et al. | 128/314 |

(Continued)

FOREIGN PATENT DOCUMENTS

| DE | 459 483 | 5/1928 |
|---|---|---|
| EP | 0 115 388 A1 | 8/1984 |

(Continued)

OTHER PUBLICATIONS

Written Opinion corresponding to International Patent Application No. PCT/US2006/030180, European Patent Office, dated Apr. 23, 2007, 8 pages.

(Continued)

*Primary Examiner* — Ryan Severson
*Assistant Examiner* — David Eastwood
(74) *Attorney, Agent, or Firm* — Nixon Peabody LLP (57) ABSTRACT

A lancing mechanism is adapted to move between a resting, cocking and a puncture position. The lancing mechanism comprises a lancet holder adapted to receive a lancet, a shaft attached to the lancet holder, at least one drive spring and at least one damping spring. The drive spring surrounds at least a portion of the shaft and drives the lancing mechanism from the cocking position to the puncture position. The damping spring moves the lancing mechanism from the puncture position to the resting position. The drive spring is located at least partially within the damping spring.

8 Claims, 7 Drawing Sheets

(56) References Cited

U.S. PATENT DOCUMENTS

| | | | |
|---|---|---|---|
| 4,553,541 A | 11/1985 | Burns | 128/314 |
| 4,627,445 A | 12/1986 | Garcia et al. | 128/770 |
| 4,637,403 A | 1/1987 | Garcia et al. | 128/770 |
| 4,653,513 A * | 3/1987 | Dombrowski | 600/578 |
| 4,735,203 A | 4/1988 | Ryder et al. | 128/314 |
| D297,459 S | 8/1988 | Heiland et al. | D24/28 |
| 4,787,398 A | 11/1988 | Garcia et al. | 128/770 |
| RE32,922 E | 5/1989 | Levin et al. | 128/314 |
| 4,924,879 A | 5/1990 | O'Brien | 128/770 |
| 4,976,724 A | 12/1990 | Nieto et al. | 606/182 |
| 4,990,154 A | 2/1991 | Brown et al. | 606/192 |
| 5,074,872 A | 12/1991 | Brown et al. | 606/182 |
| D332,490 S | 1/1993 | Brown et al. | D24/130 |
| 5,196,025 A | 3/1993 | Ranalletta et al. | 606/182 |
| 5,231,993 A | 8/1993 | Haber et al. | 128/770 |
| 5,267,963 A | 12/1993 | Bachynsky | 604/134 |
| 5,279,294 A | 1/1994 | Anderson et al. | 128/633 |
| 5,304,193 A | 4/1994 | Zhadanov | 606/182 |
| 5,318,583 A | 6/1994 | Rabenau et al. | 606/182 |
| 5,320,607 A | 6/1994 | Ishibashi | 604/115 |
| 5,350,392 A | 9/1994 | Purcell et al. | 606/182 |
| 5,527,334 A | 6/1996 | Kanner et al. | 606/182 |
| 5,575,777 A | 11/1996 | Cover et al. | 604/198 |
| 5,628,764 A | 5/1997 | Schraga | 606/182 |
| D393,716 S | 4/1998 | Brenneman et al. | D24/147 |
| D393,717 S | 4/1998 | Brenneman et al. | D24/147 |
| 5,741,288 A | 4/1998 | Rife | 606/181 |
| 5,797,942 A | 8/1998 | Schraga | 606/182 |
| 5,868,772 A | 2/1999 | LeVaughn et al. | 606/181 |
| 5,916,230 A | 6/1999 | Brenneman et al. | 606/172 |
| 5,951,492 A | 9/1999 | Douglas et al. | 600/583 |
| 5,951,493 A | 9/1999 | Douglas et al. | 600/583 |
| 5,954,738 A | 9/1999 | LeVaughn et al. | 606/181 |
| 6,022,366 A | 2/2000 | Schraga | 606/181 |
| 6,045,567 A | 4/2000 | Taylor et al. | 606/181 |
| 6,048,352 A | 4/2000 | Douglas et al. | 606/181 |
| 6,050,977 A | 4/2000 | Adams | 604/195 |
| 6,071,250 A * | 6/2000 | Douglas et al. | 600/583 |
| 6,090,078 A | 7/2000 | Erskine | 604/198 |
| 6,090,124 A | 7/2000 | Weekes | 606/182 |
| 6,093,156 A | 7/2000 | Cunningham et al. | 600/573 |
| 6,099,484 A | 8/2000 | Douglas et al. | 600/583 |
| 6,152,942 A | 11/2000 | Brenneman et al. | 606/181 |
| 6,156,051 A | 12/2000 | Schraga | 606/181 |
| 6,168,606 B1 | 1/2001 | Levin et al. | 606/181 |
| 6,197,040 B1 | 3/2001 | LeVaughn et al. | 606/182 |
| 6,210,421 B1 | 4/2001 | Böcker et al. | 606/182 |
| 6,231,531 B1 | 5/2001 | Lum et al. | 601/46 |
| 6,283,982 B1 | 9/2001 | LeVaughn et al. | 606/172 |
| 6,306,152 B1 | 10/2001 | Verdonk et al. | 606/182 |
| 6,322,574 B1 | 11/2001 | Lloyd et al. | 606/181 |
| 6,364,889 B1 | 4/2002 | Kheiri et al. | 606/181 |
| 6,409,740 B1 | 6/2002 | Kuhr et al. | 606/182 |
| 6,419,661 B1 | 7/2002 | Kuhr et al. | 604/207 |
| 6,432,120 B1 | 8/2002 | Teo | 606/182 |
| 6,451,040 B1 | 9/2002 | Purcell | 606/181 |
| 6,514,270 B1 | 2/2003 | Schraga | 606/182 |
| 6,537,292 B1 | 3/2003 | Lee | 606/182 |
| 6,561,989 B2 | 5/2003 | Whitson | 600/573 |
| 6,602,268 B2 | 8/2003 | Kuhr et al. | 606/181 |
| 6,607,543 B2 | 8/2003 | Purcell et al. | 606/181 |
| 6,749,618 B2 | 6/2004 | Levaughn et al. | 606/182 |
| 6,752,817 B2 | 6/2004 | Flora et al. | 606/181 |
| 6,837,858 B2 | 1/2005 | Cunningham et al. | 600/573 |
| 7,144,404 B2 | 12/2006 | Whitson et al. | 606/181 |
| 7,238,192 B2 | 7/2007 | List et al. | 606/182 |
| 7,303,573 B2 | 12/2007 | D'Agostino | 606/181 |
| 7,842,059 B2 * | 11/2010 | Rutynowski | 606/181 |
| 2002/0022789 A1 | 2/2002 | Perez et al. | 600/573 |
| 2003/0171696 A1 | 9/2003 | Dosmann | 600/583 |
| 2003/0171699 A1 | 9/2003 | Brenneman | 600/584 |
| 2003/0216767 A1 | 11/2003 | List et al. | 606/181 |
| 2004/0059256 A1 | 3/2004 | Perez | 600/583 |
| 2004/0087990 A1 * | 5/2004 | Boecker et al. | 606/181 |
| 2004/0248312 A1 | 12/2004 | Vreeke et al. | 436/95 |
| 2005/0038465 A1 * | 2/2005 | Shraga | 606/182 |
| 2005/0085840 A1 | 4/2005 | Yi et al. | 606/182 |
| 2006/0247671 A1 * | 11/2006 | LeVaughn | 606/182 |
| 2008/0039885 A1 * | 2/2008 | Purcell | 606/182 |

FOREIGN PATENT DOCUMENTS

| | | |
|---|---|---|
| EP | 0 204 892 A2 | 12/1986 |
| EP | 0 894 471 A2 | 2/1999 |
| EP | 0 898 936 A2 | 3/1999 |
| EP | 0 958 783 A1 | 11/1999 |
| EP | 1 541 088 A1 | 6/2005 |
| WO | WO 02/100278 A1 | 12/2002 |
| WO | WO 2004/103178 A1 | 12/2004 |
| WO | WO 2005/001418 A2 | 1/2005 |
| WO | WO 2005009238 A1 * | 2/2005 |
| WO | WO 2006/046477 A2 | 5/2005 |
| WO | WO 2005/077275 A1 | 8/2005 |
| WO | WO 2006/031535 A2 | 4/2006 |

OTHER PUBLICATIONS

International Search Report corresponding to International Patent Application No. PCT/US2006/030180, European Patent Office, dated Apr. 23, 2007, 5 pages.

* cited by examiner

LANCING DEVICE

CROSS-REFERENCE TO RELATED APPLICATIONS

This application is a U.S. national stage of International Application No. PCT/US2006/030180, filed Aug. 3, 2006, which claims the benefit of U.S. Provisional Application No. 60/705,349 filed on Aug. 4, 2005, which is incorporated by reference in its entirety.

FIELD OF THE INVENTION

The present invention relates generally to lancing devices and, more particularly, to a multi-spring, compact lancing device having at least one of the springs located within a second of the springs.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. The whole blood sample may then be used to determine the glucose concentration of an individual. Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination.

The whole blood sample is often obtained by piercing the skin of a test subject. In addition to the pain and discomfort inherent with such a puncture, existing lancing devices may cause increased pain to many individuals by failing to properly dampen the lancet after initially piercing the skin. This may result in multiple punctures to the individual's skin, increasing the discomfort to the user. Alternatively, excessive damping can reduce the lancet's force and adversely effect the puncture depth, causing insufficient sample size and the need to lance again.

Additionally, the size of a lancing device (or integrated meter that incorporates a lancing device) is considered by a user. These devices are sometimes transported by a user in a purse or pants pocket. As such, a user may desire a smaller device that requires less space than classic devices. Thus, it would be desirable to have a lancing device and method that address these issues.

SUMMARY OF THE INVENTION

According to one embodiment of the present invention, a lancing mechanism adapted to move between a resting position, a cocking position, and a puncture position is disclosed. The lancing mechanism comprises a lancet holder, a shaft, at least one drive spring, and at least one damping spring. The lancet holder is attached to a shaft and is adapted to receive a lancet. The at least one drive spring surrounds at least a portion of the shaft. The at least one drive spring is adapted to drive the lancing mechanism from the cocking position to the puncture position. The at least one damping spring is adapted to move the lancing mechanism from the puncture position to the resting position. The at least one drive spring is located at least partially within the at least one damping spring.

According to another embodiment of the present invention, a lancing mechanism adapted to move between a resting position, a cocking position, and a puncture position is disclosed. The lancing mechanism comprises a lancet holder, a shaft, at least one damping spring, and at least one drive spring. The lancet holder is attached to the shaft and is adapted to receive a lancet. The at least one damping spring surrounds at least a portion of the shaft. The at least one damping spring is adapted to move the lancing mechanism from the puncture position to the resting position. The at least one drive spring is adapted to drive the lancing mechanism from the cocking position to the puncture position. The at least one damping spring is located at least partially within the at least one drive spring.

According to yet another embodiment of the present invention, a lancing device is disclosed. The lancing device comprises a main housing and a moveable housing. The main housing includes a spring stop and forms an inner cavity enclosing a portion of a lancing mechanism. The lancing mechanism includes a lancet holder adapted to receive a lancet and a shaft attached to the lancet holder. The lancing mechanism further includes at least one drive spring detached from the spring stop. The at least one drive spring is adapted to drive the lancing mechanism from a cocking position to a puncture position. The lancing mechanism further includes at least one damping spring attached to the spring stop. The at least one damping spring is adapted to move the lancing mechanism from the puncture position to a resting position. The movable housing is adjacent the main housing and is adapted to move the lancing mechanism from the resting position to the cocking position.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 1b is a bottom exploded view of the lancing device of FIG. 1a.

DESCRIPTION OF ILLUSTRATED EMBODIMENTS

The present invention is directed to a lancet-release mechanism adapted to be incorporated into a stand-alone lancing device or into a lancing device that is incorporated into a meter or similar testing device. The lancing device is adapted to receive a lancet for use in drawing a body fluid from a test subject. The body fluid generally contains at least one analyte that may then be examined to determine its concentration in the body fluid sample.

Lancing devices and lancets may be used to produce a blood or body fluid sample from a test subject. This sample may then be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin $A_{1C}$, fructose, lactate, or bilirubin.

Figure 1A:
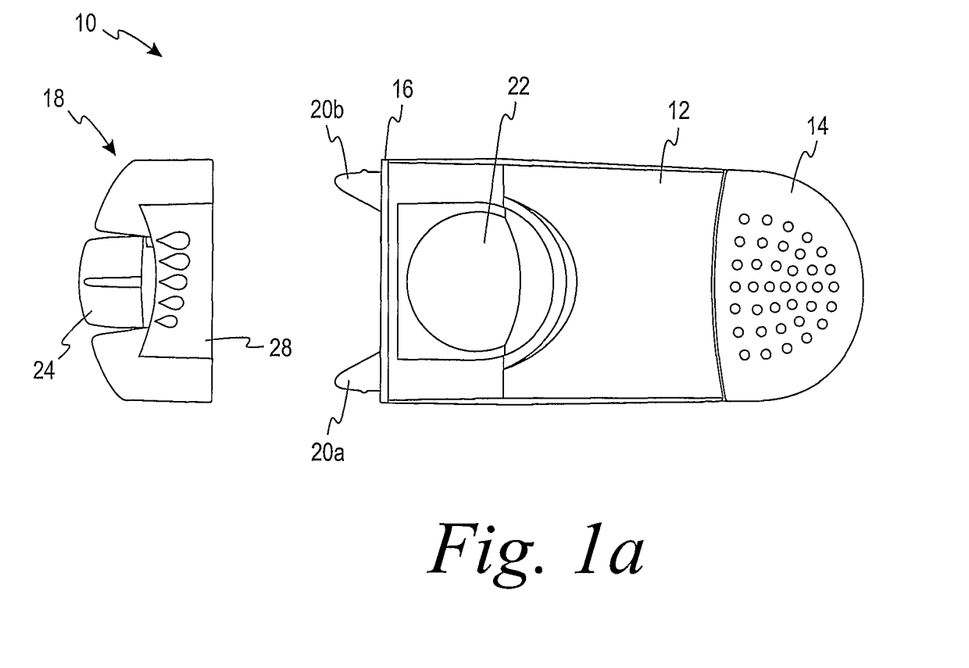
FIG. 1a is a top exploded view of a lancing device, according to one embodiment of the present invention.
Figure 1B:
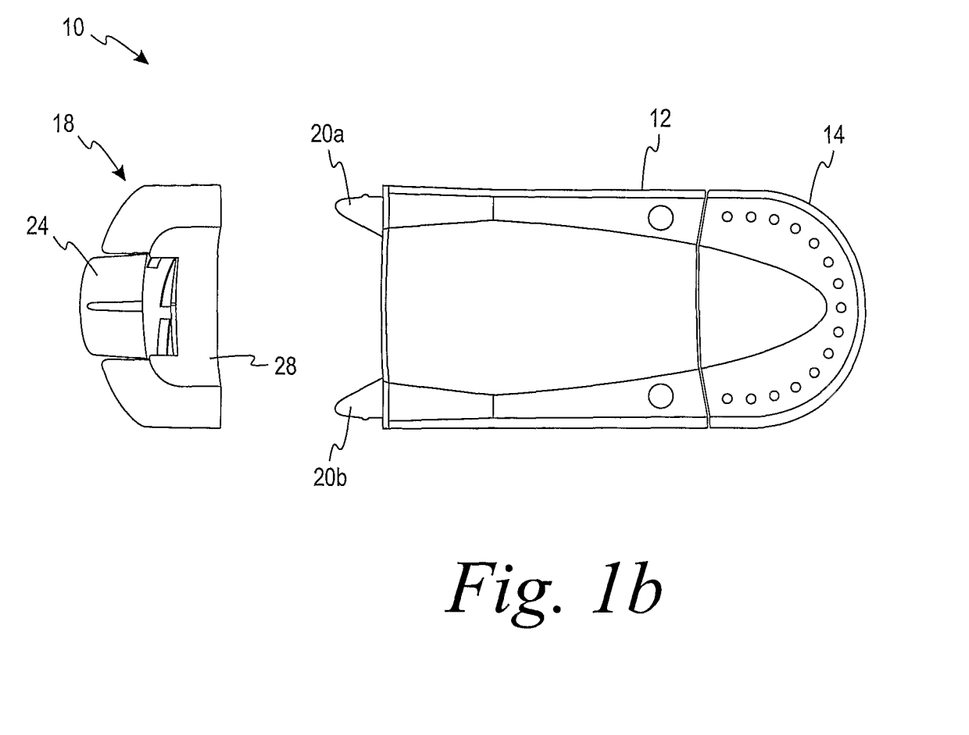
Figure 2:
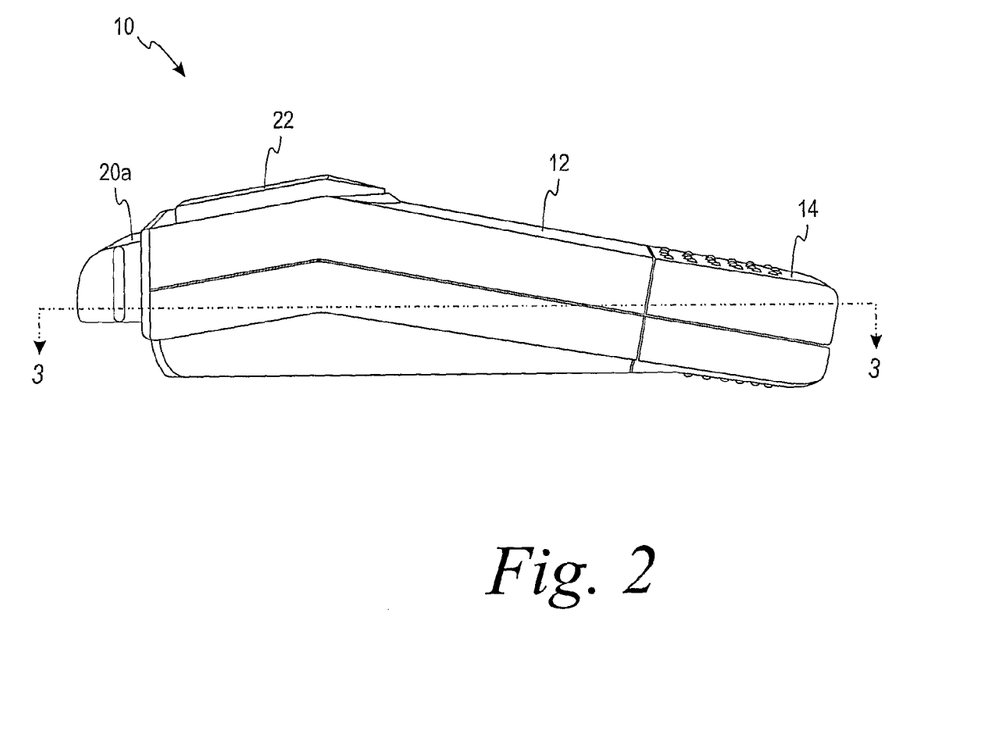
FIG. 2 is a side view of the lancing device of FIG. 1a-b.

Turning now to the drawings and initially to FIGS. 1-2, a lancing device 10 for obtaining a fluid sample from a test subject is illustrated, according to one embodiment of the present invention. The lancing device 10 has a main housing 12 and a movable housing 14 that is movable relative to the main housing 12. The main housing 12 and the movable housing 14 each forms an inner cavity, respectively. An endcap support 16 is connected to the main housing 12 on the testing end of the lancing device 10. An endcap 18 may be removably attached to the endcap support 16. When attached, the endcap 18 is retained on the endcap support 16 by a pair of support arms 20a-b integrally formed with the endcap support 16.

Figure 5:
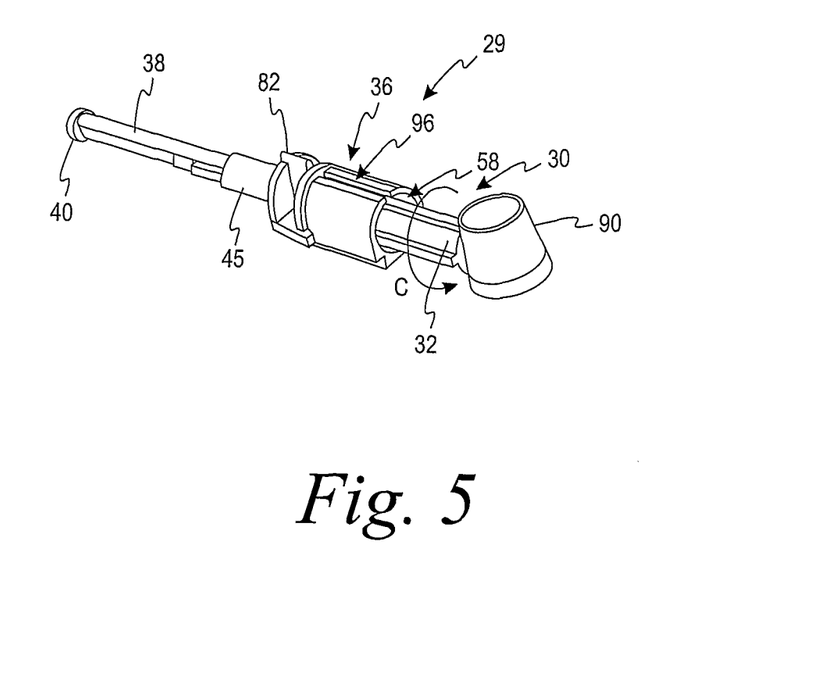
FIG. 5 is a perspective view of a lancing mechanism, according to one embodiment of the present invention.

To use the lancing device 10, the movable housing 14 is pulled away from the main housing 12 to move an internal lancing mechanism 29 (as best illustrated in FIG. 5) to a cocked position, and then a pushbutton 22 (FIG. 1) is pushed to actuate the lancing mechanism 29 so that a sharp tip of a lancet is forced through an aperture (not shown) in the endcap 18. The lancing device 10 may be provided with a number of different endcaps 18, each having a different width, to facilitate the formation of skin punctures of various depths. Alternatively, the endcap 18 may include an adjustable dial 24 for allowing punctures of different depths to be performed utilizing a single endcap 18.

Figure 3:
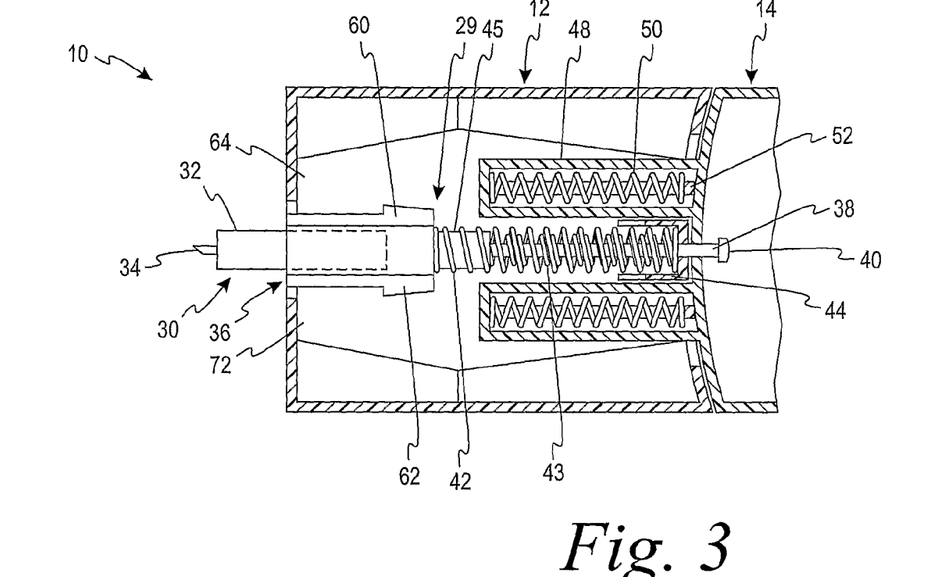
FIG. 3 is a partial, cross-sectional, top view of the lancing device of FIG. 2 in a resting position.
Figure 4:
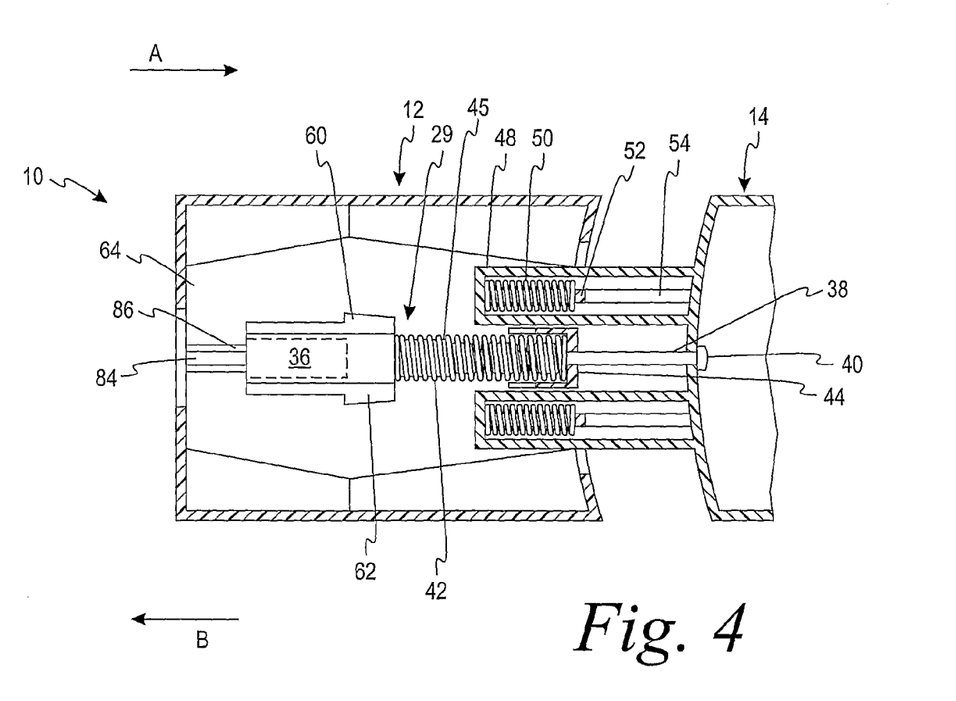
FIG. 4 is a partial, cross-sectional, top view of the lancing device of FIG. 2 in a cocking position.

Turning now to FIG. 3, a cross-sectional view of a portion of the lancing device 10 is illustrated with the endcap 18 and endcap support 16 not shown. A lancet assembly 30 having a lancet body 32 and a lance 34 (FIG. 3) is received within an internal cylindrical aperture 58 (FIG. 5) formed in a generally cup-shaped lancet holder 36. The lancet holder 36 includes one or more angled stop member. In the illustrated embodiment (FIG. 3), the lancet holder 36 includes two angled stop members 60, 62 that are located on opposite sides of the lancet holder 36. As also shown in FIG. 5, the lancet holder 36 is connected to an elongated shaft 38 by being integrally formed therewith. The shaft 38 has an enlarged end 40 that is supported within the movable housing 14. As shown in FIGS. 3 and 4, at least one spring is disposed around the shaft 38 between the lancet holder 36 and a spring stop 44 integrally formed with the main housing 12.

As illustrated in FIGS. 3-4, a drive spring 43 is provided according to some embodiments. The drive spring 43 is adapted to engage the lancet holder 36 and move the lancing mechanism 29 from the cocked position to the puncture position. According to one embodiment, the drive spring 43 is located within a damping spring 42. The damping spring 42 is adapted to dampen the lancing mechanism 29 as the lancing mechanism 29 returns from the puncture position to the resting position. The drive spring 43 has a diameter that is sufficiently small to insert into a casing 45 extending from the lancet holder 36. The casing 45 is adapted to separate at least a portion of the drive spring 43 from at least a portion of the damping spring 42. It should be noted at this point that in various embodiments of the present invention, the quantity and location of the damping and drive springs can vary. The operation and configuration of several of these embodiments will be explained in greater detail with respect to FIGS. 6-8b.

Referring still to FIGS. 3-4, the movable housing 14 has a pair of elongate spring trays 48 integrally formed therewith. A return spring 50 is disposed within each of the spring trays 48, a first end of each return spring 50 being disposed against an internal surface of the spring tray 48 and a second end of each return spring 50 being disposed against a spring stop 52 integrally formed with the main housing 12. The spring stops 52 extend into the spring trays 48 through an elongate slot 54 (see FIG. 4) formed in the bottom portion of each tray 48.

FIG. 3 illustrates the interior of the lancing device 10 when the lancing device 10 is not in use. In this position, the lancet holder 36 is disposed in a resting position between a puncture position and a cocked position. FIG. 4 illustrates the interior of the lancing device 10 (the lancet assembly 30 is not shown) when the lancet holder 36 is in a cocked position in which the movable housing 14 has been pulled away from the main housing 12.

Referring to FIG. 4, to move the lancet holder 36 from its resting position to its cocked position, the movable housing 14 is pulled away from the main housing 12 in the direction of Arrow A. The movable housing 14 continues to be pulled—against the force of the drive spring 43—until the angled stop members 60, 62 formed on the lancet holder 36 move past (to the right of as illustrated in FIG. 4) at least one retaining (not shown) formed on the housing side of the push button 22. The at least one retaining arm extends into the housing 12. The at least one retaining arm is biased so that it makes contact with one or more of the angled stop members 60, 62 formed on the lancet holder 36. A spring mechanism—for example, an elastically-deformable foam material—may be disposed between the pushbutton 22 and a portion of the main housing 12 to bias the pushbutton 22 to its non-actuated position, wherein the at least one retaining arm is able to engage one or both of the angled stop members 60, 62.

When in that cocked position, movement of the lancet holder 36 in the direction of Arrow B due to the drive spring 43 is inhibited because of the contact between the at least one retaining arm and the angled stop members 60, 62. After the lancet holder 36 is placed in the cocked position, the user allows the return springs 50 to force the movable housing 14 back to its initial position adjacent the main housing 12.

The lancet holder 36 is guided between its resting and cocked positions by a guide rib 82 (FIG. 5) formed on the bottom portion of the lancet holder 36 that rides within a groove 84 (FIG. 4) formed between a pair of raised guide rails 86 formed in a bottom interior portion of the main housing 12.

To perform a puncture on a test subject's skin, the endcap 18 is attached to the lancing device 10. The lancet holder 36 may be in the cocked position at the time the endcap 18 is attached or may be cocked once the endcap 18 is in position. The endcap 18 is then placed firmly against the skin where the puncture is to be made, and the pushbutton 22 is depressed. Depressing the pushbutton 22 causes the at least one retaining arm (not shown) to release the angled stop members 60, 62 formed on the lancet holder 36. Thus, the lancet holder 36 is no longer prevented from moving in the direction of Arrow B by the contact of the at least one retaining arm with one or both of the angled stop members 60, 62.

Upon release of the lancet holder 36 as described above, the drive spring 43 will force the lancet holder 36 in the direction of Arrow B until the sharp point of the lance 34 (FIG. 3) passes through the aperture (not shown) in the endcap 18 to make the puncture. When the puncture is made, the damping spring 42 will be in a stretched position, and after the puncture is made, the contraction of the damping spring 42 draws the lancet holder 36 back towards its resting position shown in FIG. 3.

Turning now to FIG. 5, a perspective view of the lancing mechanism 29 is illustrated, according to one embodiment of the present invention. The lancet mechanism 29 includes the lancet holder 36 adapted to receive the lancet assembly 30. As illustrated in FIG. 5, the lancet assembly 30 is disposed within the generally cylindrical aperture formed in the lancet holder 36. The lancet assembly 30 is shown with a protective cap 90 that has a portion that is integrally formed with the lancet body 32 and which covers the sharp point of the lance 34. Prior to using the lancing device 10, the lancet body 32 of a new lancet assembly 30 is inserted into the cylindrical aperture disposed in the lancet holder 36, and then the protective cap 90 is twisted off of the lancet assembly 30, in the direction of the Arrow C shown in FIG. 5.

Figure 6:
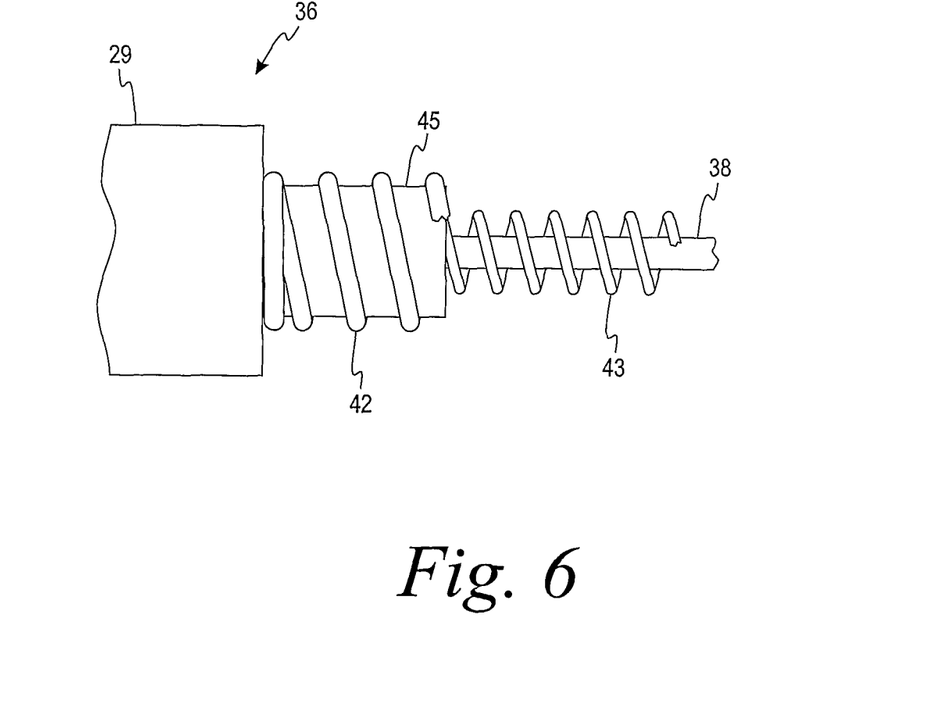
FIG. 6 is partial-perspective view of the lancing mechanism of FIG. 5 with a drive spring and a damping spring surrounding a shaft, according to one embodiment.

Referring also to FIG. 6, a portion of the lancing mechanism 29 illustrated in FIG. 5 is illustrated according to one embodiment. The shaft 38 of the lancing mechanism 29 is partially surrounded by both the drive spring 43, the damping spring 42, and the casing 45. The drive spring 43 is located within the damping spring 42 and is partially separated from the damping spring 42 by the casing 45. The damping spring 42 is attached to the lancet holder 36 while the drive spring 43 may or may not be attached to the lancet holder 36, in alternative embodiments.

Turning now to FIGS. 7a-8b, damping systems that can be incorporated into the above-described lancing device 10 are further described according to the various embodiments of the present invention. Such damping systems assist in preventing or inhibiting the lancing mechanism 29 from causing a second, unintended skin puncture to be made by the lancet assembly 30. The damping system includes a plurality of springs in which a first spring is located within at least a second spring. For the purposes of this disclosure, the term "within" is defined as either "partially enclosed by" (such as the two-spring embodiment described above) or "between" (such as the three-spring embodiment described below with respect to FIGS. 8a-b).

Figure 7A:
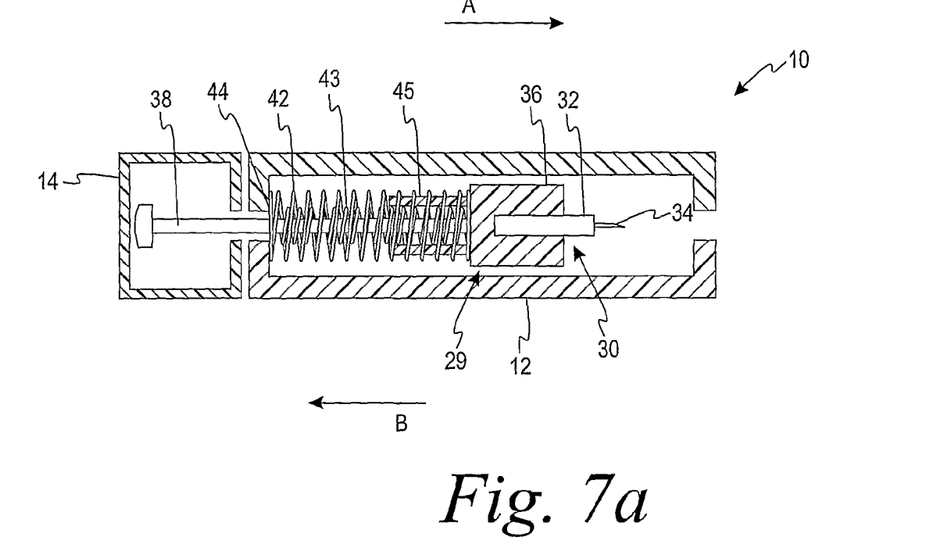
FIG. 7a is a schematic cross-sectional view of a lancing device in a cocking position, according to one embodiment of the present invention.
Figure 7B:
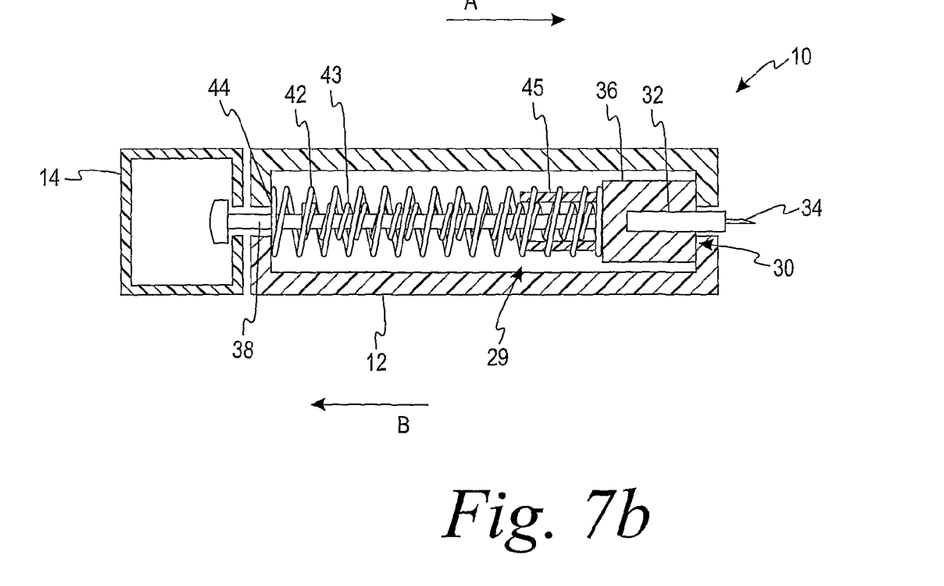
FIG. 7b is a schematic cross-sectional view of the lancing device of FIG. 7a in a puncture position.
Figure 7C:
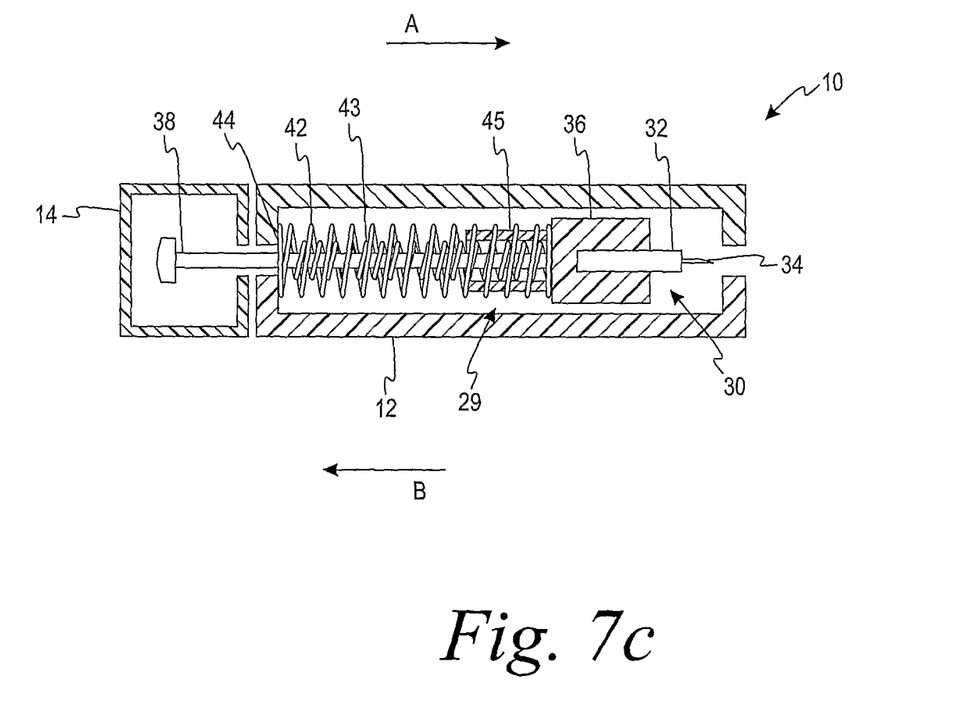
FIG. 7c is a schematic cross-sectional view of the lancing device of FIG. 7a in a resting position.

Turning now to FIGS. 7a-c, a damping system incorporating a single damping spring 42 and a single drive spring 43 is illustrated. The damping system is incorporated into the lancing device 10 and is adapted to both drive the lancing mechanism 29 from the cocked position (illustrated in FIG. 7a) to the puncture position (illustrated in FIG. 7b) and to damp the lancing mechanism 29 as the lancing mechanism 29 moves from the puncture position to the resting position (illustrated in FIG. 7c). To ensure that the lancing mechanism 29 reaches the puncture position when the lancing device 10 is fired, the spring rate of the drive spring 43 is much higher than the spring rate of the damping spring. 42.

The damping spring 42 is attached to both the lancet holder 36 and the spring stop 44. The damping spring 42 is an extension spring such that the firing of the lancing device 10 causes the drive spring 43 to move the lancing mechanism 29 from the cocked position to the puncture position. This movement extends the damping spring 42 from its resting state. After the drive spring 43 has substantially decompressed, the return force of the extended damping spring 42 overtakes the drive force of the drive spring 43 and causes the lancing mechanism 29 to return to the resting position. The drive spring 43 can be attached to the lancet holder 36 or may be entirely free-floating.

In the embodiment illustrated in FIG. 7b, the drive spring 43 is attached to the lancet holder 36 only. Thus, as the drive spring 43 fully decompresses it breaks contact with the spring stop 44. This allows the damping spring 42 to return the lancing mechanism 29 to the resting position without substantial assistance or impedance by the drive spring 43. As illustrated in FIG. 7c, the lancing mechanism 29 is in the resting position when the damping spring 42 has caused the drive spring 43 to contact the spring stop 44 without being substantially compressed.

In alternative embodiments of the present invention, the damping spring 42 and the drive spring 43 are switched such that the damping spring 42 is located within the drive spring 43 with the drive spring 43 surrounding both the damping spring 42 and a portion of the casing 45. In these embodiments, the spring rate of the drive spring 43 remains greater than the spring rate of the damping spring 43. The spring rate of the springs may be adjusted by, for example, using different materials, different number of coils, different coil sizes, etc.

Figure 8A:
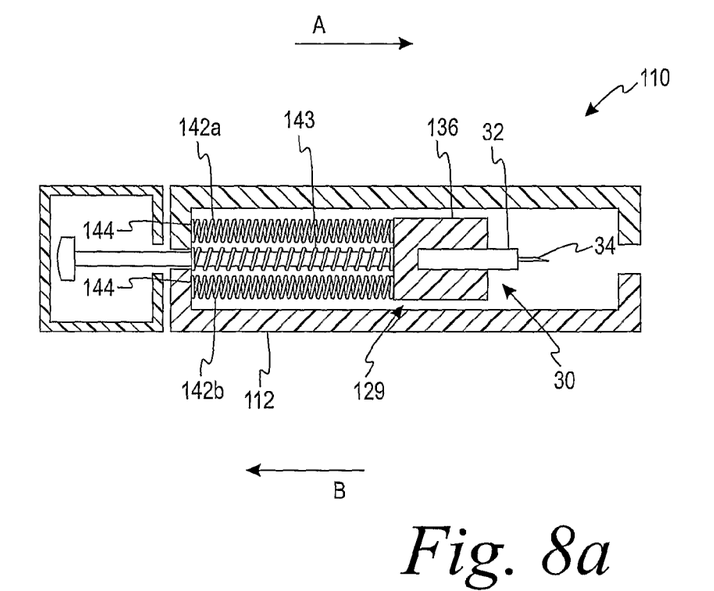
FIG. 8a is a schematic cross-sectional view of a lancing device having a plurality of damping springs, according to one embodiment.
Figure 8B:
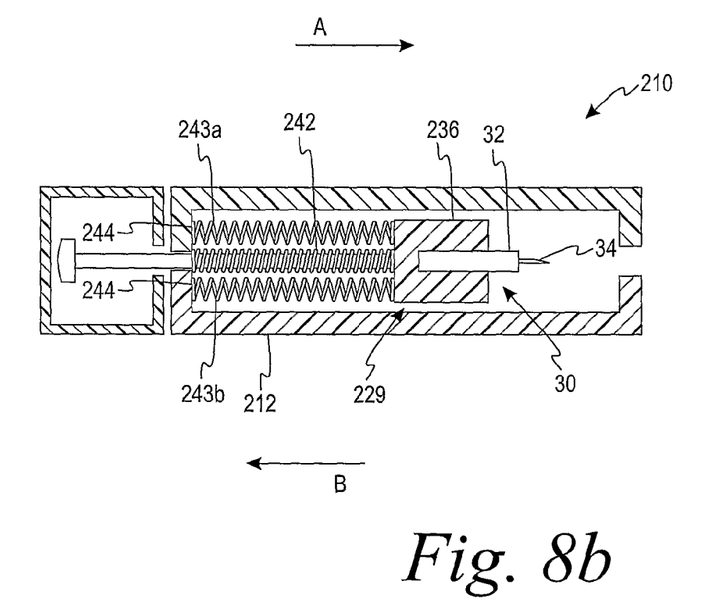
FIG. 8b is a schematic cross-sectional view of a lancing device having a plurality of drive springs, according to another embodiment.

Turning now to FIGS. 8a-b, a damping system including a plurality of damping springs or a plurality of drive springs is incorporated into a lancing device. In the embodiment of FIG. 8a, a lancing device 110 includes a drive spring 143 located within a plurality of damping springs 142a,b. Similar to the above embodiment, the damping springs 142a,b are attached to both a lancet holder 136 and a spring stop 144, while the drive spring 143 is attached only to the lancet holder 136. In alternative embodiments, the drive spring 143 is free-floating along a shaft (not shown) and is not attached to the lancet holder 136. In the embodiment illustrated in FIG. 8a, the spring rate of each of the damping springs 142a,b is substantially lower than the spring rate of the drive spring 142. The operation of the lancing device 110 is substantially similar to that described above with respect to FIGS. 7a-c except that, in the embodiment of FIG. 8a, a plurality of damping springs 142a,b is used to return a lancing mechanism 129 from the puncture position to the resting position.

Referring now to FIG. 8b, a lancing device 210 includes a damping spring 242 located within a plurality of drive springs 243a,b. Similar to the above embodiments, the damping spring 242 is attached to both a lancet holder 236 and a spring stop 244, while each of the plurality of drive springs 243 is attached only to the lancet holder 236. In this embodiment, the spring rate for each of the plurality of drive springs 243a,b and the spring rate for the damping spring 242 may be substantially equal. As should be apparent, if the spring rate is approximately equal for each of the three springs, the multiplicity of the drive springs 243a,b helps to ensure that a sufficient force is applied to a lancing mechanism 229 to move the lancing mechanism 229 from the cocked position to the puncture position.

ALTERNATIVE EMBODIMENT A

A lancing mechanism adapted to move between a resting position, a cocking position, and a puncture position comprising:
  a lancet holder adapted to receive a lancet;
  a shaft attached to the lancet holder;

at least one drive spring surrounding at least a portion of the shaft, the at least one drive spring being adapted to drive the lancing mechanism from the cocking position to the puncture position;

at least one damping spring being adapted to move the lancing mechanism from the puncture position to the resting position, the at least one drive spring being located at least partially within the at least one damping spring.

ALTERNATIVE EMBODIMENT B

The lancing mechanism of Alternative Embodiment A, wherein the at least one damping spring is two damping springs.

ALTERNATIVE EMBODIMENT C

The lancing mechanism of Alternative Embodiment B, wherein the drive spring is located between the two damping springs.

ALTERNATIVE EMBODIMENT D

The lancing mechanism of Alternative Embodiment A, wherein the drive spring is partially enclosed by the damping spring.

ALTERNATIVE EMBODIMENT E

The lancing mechanism of Alternative Embodiment A, wherein a spring rate of the drive spring is greater than a spring rate of the damping spring.

ALTERNATIVE EMBODIMENT F

A lancing mechanism adapted to move between a resting position, a cocking position, and a puncture position comprising:

a lancet holder adapted to receive a lancet;

a shaft attached to the lancet holder;

at least one damping spring surrounding at least a portion of the shaft, the at least one damping spring being adapted to move the lancing mechanism from the puncture position to the resting position;

at least one drive spring being adapted to drive the lancing mechanism from the cocking position to the puncture position, the at least one damping spring being located at least partially within the at least one drive spring.

ALTERNATIVE EMBODIMENT G

The lancing device of Alternative Embodiment F, wherein the at least one drive spring is two drive springs.

ALTERNATIVE EMBODIMENT H

The lancing device of Alternative Embodiment G, wherein a spring rate of each of the two drive springs is approximately the same as a spring rate of the at least one damping spring.

ALTERNATIVE EMBODIMENT I

The lancing device of Alternative Embodiment H, wherein an overall spring rate of the two drive springs is substantially greater than the spring rate of the at least one damping spring.

ALTERNATIVE EMBODIMENT J

The lancing device of Alternative Embodiment G, wherein the at least one damping spring is located between the two drive springs.

ALTERNATIVE EMBODIMENT K

The lancing device of Alternative Embodiment F, wherein the at least one damping spring and the at least one drive spring are attached to the lancet holder.

ALTERNATIVE EMBODIMENT L

A lancing device comprising:

a main housing including a spring stop, the main housing forming an inner cavity enclosing a portion of a lancing mechanism, the lancing mechanism including a lancet holder adapted to receive a lancet and a shaft attached to the lancet holder, the lancing mechanism further including at least one drive spring being detached from the spring stop, the at least one drive spring being adapted to drive the lancing mechanism from a cocking position to a puncture position, the lancing mechanism further including at least one damping spring being attached to the spring stop, the at least one damping spring being adapted to move the lancing mechanism from the puncture position to a resting position; and a movable housing adjacent the main housing, the movable housing being adapted to move the lancing mechanism from the resting position to the cocking position.

ALTERNATIVE EMBODIMENT M

The lancing device of Alternative Embodiment L, wherein the at least one drive spring at least partially surrounds the shaft of the lancing mechanism.

ALTERNATIVE EMBODIMENT N

The lancing device of Alternative Embodiment M, wherein the at least one damping spring at least partially surrounds both the at least one drive spring and the shaft of the lancing mechanism.

ALTERNATIVE EMBODIMENT O

The lancing device of Alternative Embodiment M, wherein the at least one drive spring is free-floating along the shaft of the lancing mechanism.

ALTERNATIVE EMBODIMENT P

The lancing device of Alternative Embodiment L, wherein the lancing mechanism further includes a casing extending from the lancet holder and surrounding at least a portion of the shaft, the casing adapted to partially separate the at least one drive spring from the at least one damping spring.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A lancing device comprising:

a main housing including a spring stop, the spring stop being adjacent to a first end of the main housing, the main housing forming an inner cavity enclosing a portion of a lancing mechanism, the lancing mechanism including a lancet holder adapted to receive a lancet and a shaft fixed to the lancet holder, the lancet holder being spaced from the spring stop, the lancing mechanism further including at least one drive spring being detached from the spring stop, the at least one drive spring being adapted to drive the lancing mechanism from a cocking position to a puncture position, the lancing mechanism further including two damping springs being attached to and positioned between each of the lancet holder and the spring stop, the two damping springs being adapted to move the lancing mechanism from the puncture position to a resting position; and a movable housing adjacent the main housing, the movable housing being adapted to move the lancing mechanism from the resting position to the cocking position.

2. The lancing device of claim 1, wherein a spring rate of the at least one drive spring is greater than a spring rate of each of the two damping springs.

3. The lancing device of claim 1, wherein the at least one drive spring at least partially surrounds the shaft of the lancing mechanism.

4. The lancing device of claim 3, wherein the two damping springs at least partially surround both the at least one drive spring and the shaft of the lancing mechanism.

5. The lancing device of claim 3, wherein the at least one drive spring is free-floating along the shaft of the lancing mechanism.

6. The lancing device of claim 1, wherein the at least one drive spring is attached to the lancet holder.

7. The lancing device of claim 1, wherein the at least one drive spring is between the two damping springs during the resting position, the cocking position, and the puncture position.

8. The lancing device of claim 1, wherein the lancet holder is adjacent to a second end of the main housing opposite the first end of the main housing when the lancing mechanism is in the puncture position.

\* \* \* \* \*

UNITED STATES PATENT AND TRADEMARK OFFICE
CERTIFICATE OF CORRECTION

| | | |
|---|---|---|
| PATENT NO. | : 8,617,195 B2 | Page 1 of 1 |
| APPLICATION NO. | : 11/989085 | |
| DATED | : December 31, 2013 | |
| INVENTOR(S) | : Tieming Ruan et al. | |

It is certified that error appears in the above-identified patent and that said Letters Patent is hereby corrected as shown below:

IN THE SPECIFICATION

In Column 4, Line 38, delete "retaining (not" and insert -- retaining arm (not --, therefor.

Signed and Sealed this
Second Day of June, 2015

Michelle K. Lee
*Director of the United States Patent and Trademark Office*

UNITED STATES PATENT AND TRADEMARK OFFICE
CERTIFICATE OF CORRECTION

PATENT NO.        : 8,617,195 B2                                               Page 1 of 1
APPLICATION NO.   : 11/989085
DATED             : December 31, 2013
INVENTOR(S)       : Ruan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1663 days.

Signed and Sealed this
Twenty-second Day of September, 2015

Michelle K. Lee
*Director of the United States Patent and Trademark Office*